United States Patent [19]

Halloran

[11] Patent Number: 5,728,676
[45] Date of Patent: Mar. 17, 1998

[54] USE OF INSULIN-LIKE GROWTH FACTORS I AND II FOR INHIBITION OF INFLAMMATORY RESPONSE

[75] Inventor: Philip F. Halloran, Edmonton, Canada

[73] Assignee: Ciba-Geigy Corporation, Ardsley, N.Y.

[21] Appl. No.: 444,849

[22] Filed: May 19, 1995

Related U.S. Application Data

[62] Division of Ser. No. 302,494, Sep. 8, 1994.
[51] Int. Cl.$^6$ .................. A61K 38/00; A61K 37/26; C07K 5/00
[52] U.S. Cl. .................. 514/12; 514/3; 514/21
[58] Field of Search .................. 514/12, 21, 3

[56] References Cited

U.S. PATENT DOCUMENTS

| | | | |
|---|---|---|---|
| 4,738,921 | 4/1988 | Belagaje et al. | 435/68 |
| 4,783,524 | 11/1988 | Larsen et al. | 530/350 |
| 4,837,148 | 6/1989 | Cregg | 435/172.3 |
| 4,861,757 | 8/1989 | Antoniades et al. | 514/21 |
| 4,929,555 | 5/1990 | Cregg et al. | 435/172.3 |
| 4,988,675 | 1/1991 | Froesch et al. | 514/4 |
| 5,028,531 | 7/1991 | Ueda et al. | 435/69.4 |
| 5,106,832 | 4/1992 | Froesch et al. | 514/12 |
| 5,158,875 | 10/1992 | Miller et al. | 435/69.1 |
| 5,187,151 | 2/1993 | Clark et al. | 514/3 |
| 5,206,023 | 4/1993 | Hunziker | 424/423 |
| 5,270,300 | 12/1993 | Hunziker | 514/12 |
| 5,294,446 | 3/1994 | Schlameus et al. | 514/21 |
| 5,527,776 | 6/1996 | Carliao et al. | 514/12 |

FOREIGN PATENT DOCUMENTS

| | | |
|---|---|---|
| 120 551 | 10/1984 | European Pat. Off. |
| 123 228 | 10/1984 | European Pat. Off. |
| 128 733 | 12/1984 | European Pat. Off. |
| 135 094 | 3/1985 | European Pat. Off. |
| 155 655 | 9/1985 | European Pat. Off. |
| 264 074 | 4/1988 | European Pat. Off. |
| 303 855 | 2/1989 | European Pat. Off. |
| 434 625 | 6/1991 | European Pat. Off. |
| 436 469 | 7/1991 | European Pat. Off. |
| 478 333 | 4/1992 | European Pat. Off. |
| 560 723 | 9/1993 | European Pat. Off. |
| 85/00831 | 2/1985 | WIPO |
| 93/19085 | 9/1985 | WIPO |
| 88/03409 | 5/1988 | WIPO |
| 89/03423 | 4/1989 | WIPO |
| 90/14838 | 12/1990 | WIPO |
| 91/00357 | 1/1991 | WIPO |
| 91/04282 | 4/1991 | WIPO |
| 92/04363 | 3/1992 | WIPO |
| 92/11865 | 7/1992 | WIPO |
| 92/22311 | 12/1992 | WIPO |
| 92/22653 | 12/1992 | WIPO |
| 93/08826 | 5/1993 | WIPO |
| 93/10806 | 6/1993 | WIPO |
| 93/11240 | 6/1993 | WIPO |
| 93/25219 | 12/1993 | WIPO |
| 93/25227 | 12/1993 | WIPO |

OTHER PUBLICATIONS

Shoskes et al., "Ischemic injury induces atlered MHC gene expression in kidney by an interferon–gamma–dependent pathway," *Transplantation Proceedings* 23(1):599–601 (1991).
Feinberg and Volgelstein, *Anal Biochem*, (1983) 132:6.
Gaillardin, *Curr. Genet.*, (1985) 10:49.
Geraughty, *Curr. Opin. Immunol.*, (1993) 5:3.
Gleeson, *J. Gen. Microbiol.*, (1986) 32:3459.
Glisin, *Biochemistry*, (1974) 13:2633.
Gray, *PNAS (USA)* (1983) 80:5842.
Miller, *PNAS (USA)* (1992) 89:11876.
Matejka, *Kidney International* (1992) 42:1113.
Gluckman, *Biochem. Biophys. Res. Comm.* (1992) 182:593.
Middleton, *Annals of Rheumatic Diseases* (1992) 51:440.
Moskowitz, *J. of Rheumatology, supp.* (1991) 27:147.
Dequeker *Arthritis and Rheumatism* (1993) 36:1702.
Hampton, *J. of Biol. Chem.* (1989) 264:19155.
Denko, *J. of Rheumatology* (1990) 17:1217.
Ballance, *Biochem. Biophys. Res. Comm.*, (1983) 112:284.
Barr, *Bio/Technology*, (1987) 5:486.
Beach, *Nature*, (1981) 300:706.
Beier, *Nature*, (1982) 300:724.
Brake, *PNAS (USA)*, (1984) 81:4642.
Buergisser, *Biochem. Biophys. Res. Comm.* (1990) 169:832–839.
Nolan et al., *Cell Regulation*, (1990) 1:197–213.
Ding *J. of Clin. Invest.* (1993) 91:2281.
Hinnen, *PNAS (USA)*, (1978) 75:1929.
Li, *PNAS*, (1983) 80:2216–2220.
Rinderknecht, *J Biol Chem*, (1978) 253:2769.
Rinderknecht, *FEBS Letters*, (1978) 89:283.
Rogachefsky, *Osteoarthritis and Cartilage*, (1993) 1:105–114.
Urdea, *PNAS (USA)*, (1983) 80:7461.
Wells, *Gene* (1985) 34:315.
Chirgwin, *Biochemistry*, (1979) 18:5294.
Cockfield, *J. Immunol* (1989) 142:1120.
Cregg, *Mol. Cell. Biol.* (1985) 5:3376.
Das, *J. Bacteriol.* (1984) 158:1165.
De Louvencourt, *J. Bacteriol.* (1983) 154:737.
Graham, *J. Gen. Virol.* (1977) 36:59.
Ito, *J. Bacteriol.* (1983) 153:163.
Kurtz, *Mol. Cell. Biol.* (1980) 23:243.
Mather, *Biol. Reprod.* (1980) 23:243.
Phillips, *New Engl. J. Med.* (1980) 302:371–380.
Reyes, *Nature* (1982) 297:598.
Roggenkamp, *Mol. Gen. Genet.* (1986) 202:302.
Salacinski, *Anal. Biochem.* (1981) 117:136.
Shoskes, *Transplantation* (1990) 49:201.
Tilburn, *Gene* (1983) 26:205.
Urlaub, *PNAS (USA)* (1980) 77:4216.
Van den Berg, *Bio/Technology* (1990) 8:135.
Yelton, *PNAS (USA)* (1984) 1981:1470.
Kelly et al., *EMBO J.* (1985) 4:475–479.
Zimmerman et al., *Gastroenterology* (1993) 105(2):399–409 abstract.

*Primary Examiner*—Cecilia J. Tsang
*Assistant Examiner*—P. Lynn Touzeau
*Attorney, Agent, or Firm*—Roberta L. Robins; Grant D. Green; Robert P. Blackburn

[57] ABSTRACT

The present invention relates to methods for using IGF as inhibitors of inflammatory response, ischemic injury, and organ rejection.

6 Claims, 5 Drawing Sheets

USE OF INSULIN-LIKE GROWTH FACTORS
I AND II FOR INHIBITION OF
INFLAMMATORY RESPONSE

This application is a divisional of application Ser. No. 08/302,494, filed Sep. 8, 1994.

BACKGROUND OF THE INVENTION

This invention relates to the use of insulin-like growth factor (IGF), including IGF-I and IGF-II, for inhibition of inflammatory response such as in rheumatoid arthritis, psoriatic arthritis, Reiter's syndrome, and other known inflammatory arthritis, as well as inflammatory bowel disease. This invention also relates to inhibition of ischemic injury and inhibition of organ rejection upon transplantation.

Insulin-like growth factors, IGF-I and IGF-II, each have a molecular weight of about 7,500 daltons. Each of IGF-I and IGF-II possesses A and B domains that are highly homologous to the corresponding domains of proinsulin. A and B domains are connected to each other by a C domain. A carboxy terminal extension, the D domain, is present in IGF but is not found in proinsulin. Both IGF-I and IGF-II are single-chain polypeptides each with 3 disulfide bridges and have a sequence identity of 49% and 47%, respectively, to human insulin A chain and B chain. Like insulin, IGF stimulate phosphorylation of specific tyrosine residues within the cytoplasmic domain of the receptors to which they bind, as described in WO 93/98826. The designation "insulin-like growth factor" was chosen to express the insulin-like effects and the insulin-like structure of these polypeptides which act as mitogens on a number of cells, as described in EP 128 733. IGF-I is a 70 amino acid peptide, while IGF-II is a 67 amino acid peptide, as described in Rinderknecht, *J Biol Chem*, (1978) 253:2769; and Rinderknecht, *FEBS Letters*, (1978) 89:283. IGF-I and IGF-II have 62% structural homology to each other. Both have been isolated from human serum.

Insulin-like growth factors are also known under the class name somatomedins, and have been identified in various animal species as polypeptides that act to stimulate growth of cells in a variety of tissues and cell types, particularly during development. Growth promoting effects of somatomedins include enhancement of cell multiplication and stimulation of cartilage proliferation, stimulation of transport of amino acids, stimulation of synthesis of RNA, DNA and protein, and stimulation of incorporation of sulfate into proteoglycan and of proline into collagen. Much mammalian postnatal growth is due to stimulation of cartilage growth by somatomedins and growth in utero may also be somatomedin-dependent.

Uses of IGF as a known stimulatory and growth promoting agent includes use for bone repair and replacement therapy, as described in EP 303 855; as a means to counteract certain harmful side effects of carcinostatic drugs, as described in JP 63-196524; and as a way to increase lactation and meat production in cattle and other farm animals, as described in U.S. Pat. No. 4,783,524.

IGF-I has also been found useful in the treatment of osteoporosis in mammals exhibiting decreased cortical bone mineral density and those exposed to drugs or environmental conditions that result in bone density reduction and potentially to an osteoporosis condition, as described in EP 560 723 and EP 436 469.

IGF-I has been administered with sodium pentosan polysulfate (PPS) to severely osteoarthritic canines with the effect of reducing the severity of the disease by lowering the levels of active neutral metalloproteinase in the cartilage. In the model of mildly osteoarthritic canines, therapeutic intervention with IGF-I and PPS together appeared to successfully maintain cartilage structure and biochemistry, while IGF alone was ineffective, as described in Rogachefsky, *Osteoarthritis and Cartilage*, (1993) 1:105–114. It would be advantageous to discover further uses for IGFs.

SUMMARY OF THE INVENTION

It is an object of the present invention to discover and provide for additional uses of IGFs. It is another object of the present invention to provide a method for inhibition of an inflammatory response such as in rheumatoid arthritis, psoriatic arthritis, Reiter's syndrome, and other known inflammatory arthritis and inflammatory bowel disease.

It is also an object of the present invention to provide a method for inhibition of ischemic injury as, for example, in acute renal tubular necrosis (ATN), ischemic injury to the heart, brain, or liver.

It is further an object of the present invention to provide a method for inhibition of organ rejection upon transplantation, including transplantation of kidney, heart, lung, liver and pancreas.

It is yet a further object of the present invention to provide a method for the treatment of rheumatoid arthritis, psoriatic arthritis, Reiter's syndrome, and other known inflammatory arthritis, as well as inflammatory bowel disease.

In accordance with one of the objects of the present invention, therefore, there is provided a method for inhibition of an inflammatory response by administering an inflammatory response inhibitory dose of IGF. In accordance with another one of the objects of the present invention, there is provided a method for the inhibition of ischemic injury by administering an ischemic injury inhibitory dose of IGF. Also, the invention provides a method for inhibiting organ rejection after transplantation by administering an organ rejection inhibitory dose of an IGF.

Further objects, features and advantages of the present invention will become apparent from the following detailed description. It should be understood, however, that the detailed description, while indicating preferred embodiments of the invention, is given by way of illustration only, since various changes and modifications within the spirit and scope of the invention will become apparent to those skilled in the art from this detailed description.

DETAILED DESCRIPTION OF THE INVENTION

This invention relates to a method for inhibiting an inflammatory response, ischemic injury, and organ rejection upon transplantation with the use of IGF-I or IGF-II. Previously, IGF-I and IGF-II have been known primarily for their stimulatory and growth-promoting effects. Unexpectedly, the inventors herein have found that IGF is also capable of inhibitory responses such as inhibiting inflammatory response, ischemic injury, and organ rejection.

The term "insulin-like growth factor" as used herein encompasses IGF-I and IGF-II in their substantially purified, native, recombinantly produced, or chemically synthesized forms, and includes biologically active fragments, analogues, muteins, including C-terminal deletion muteins, and derivatives thereof that retain IGF activity and/or ability to bind the IGF receptors, as described in, for example, EP 135 094, WO 85/00831, U.S. Pat. No. 4,738,921, WO 92/04363, U.S. Pat. No. 5,158,875, EP 123 228, and EP 128 733. An analog of IGF or an analog of the fragment includes native IGF that has been modified by one or more amino acid insertion, deletion, or substitution that does not substantially affect its properties. Preferably, the analog has increased activity compared to native IGF. More preferably, at least 2-fold increase, most preferably, at least 7–10 fold increase. For example, the analog can include conservative amino acid substitutions. An IGF analog also includes peptides having one or more peptide mimics ("peptoids"), such as those described in WO 91/04282.

An IGF mutein is polypeptide variant with one or more amino acids altered to produce a desired characteristic, such as to replace a cysteine residue with a non-disulfide bond forming amino acid. Muteins, analogues and derivatives may be generated using conventional techniques. For example, PCR mutagenesis can be used. While the following discussion refers to DNA, it is understood that the technique also finds application with RNA. An example of a PCR technique is described in WO 92/22653. Another method for making analogs, muteins, and derivatives, is cassette mutagenesis based on the technique described by Wells, *Gene*, (1985) 34:315.

An "inflammatory response" is generally characterized by increased blood flow and entry of leukocytes into the tissues, resulting in swelling, redness, elevated temperature and pain. One indication of an inflammatory response is the expression of Class I or Class II of the major histocompatibility complex ("MHC"). Class I MHC is expressed on the surface of essentially all nucleated cells, particularly lymphoid cells. Class II MHC is expressed on macrophages as part of the inflammatory response in mammals. When activated by agents such as γ-interferon, capillary endothelia and many epithelial cells express surface Class II and increased expression of Class I. The inventors herein found that administration of IGF in vivo can be effective in inhibiting inflammation. Such inhibition can be monitored, for example, by reduction in the expression of Class I or Class II MHC, or by the amount of antibody binding to Class I or Class II MHC, as described in Geraughty, *Curr. Opin. Immunol.*, (1993) 5:3; Kara C. & Glimcher, *Curr. Opin. Immunol.* (1991) 3:16; and Kurlander, *Science*, (1992) 257:678.

"Ischemic injury" resulting from decreased blood flow to an organ, includes, for example, arterial narrowing or mechanical obstruction of the blood supply. Ischemic injury in the mammal involves production of cytokines such as IL-6, IL-8 and IFN-γ. Other cytokines that may be induced by ischemic injury include the interleukins, such as IL-1, IL-2 and IL-10, colony stimulating factors (CSF), and those involved in healing and repair such as tumor necrosis factor (TNF) and transforming growth factor-beta (TGF-β). Cytokines have been documented to exert diverse effects both in vitro and in vivo, including damage to surrounding tissues in addition to healing and repair.

An "inflammatory response inhibitory dose" as used herein is a therapeutically effective amount that is sufficient to reduce or prevent a further inflammatory response. Inhibition of inflammatory response can be monitored by any conventional method. One method, for example, is to monitor the reduction in expression of Class I MHC or Class II MHC by, for example, detecting antibody binding to the MHCs. Inflammatory response is considered to have been inhibited if there is at least a 5% reduction of such response, preferably, at least a 10% reduction, more preferably, at least a 15% reduction, and most preferably, at least a 20% reduction or higher.

An "ischemic injury inhibiting dose" as used herein is a therapeutically effective amount that is sufficient to reduce or prevent a response resulting from ischemic injury. Such as response can also be monitored by conventional methods. One method, for example, is to monitor the reduction in the induction of cytokine production, such as those cytokines mentioned above. Ischemic injury is considered to have been inhibited herein if there is at least a 5% reduction of such cytokine production, preferably, at least a 10% reduction, more preferably, at least a 15% reduction, and most preferably, at least a 20% reduction or higher.

An "organ rejection inhibitory dose" as used herein is a therapeutically effective amount that is sufficient to prevent organ rejection after transplantation or to prolong the acceptance of the transplanted organ.

An "arthritic condition" is considered to have been inhibited if there is no deterioration in the cell type concerned. Typically, an arthritis inhibitory dose will further effect regeneration of the cell type, resulting in at least a 2% increase in the cell type, preferably, at least a 5% increase, more preferably, at least a 10% increase, and most preferably, at least a 15% increase or higher.

A "pharmaceutically acceptable carrier" is a carrier that is conventionally used by persons skilled in the art for administration of a therapeutic composition into a human. Such a carrier typically minimizes undesirable side effects of, for example, the induction of antibodies production, the induction of fever, etc. Suitable carriers are typically large, slowly metabolized macromolecules that includes molecules such as a protein, a polysaccharide, a polylactic acid, a polyglycolic acid, a polymeric amino acid, amino acid copolymers or an inactive virus particle. Such carriers are well known to those of ordinary skill in the art.

A "therapeutic composition" herein contains as an active ingredient either IGF-I or IGF-II or both and one or more pharmaceutically acceptable carriers, and/or one or more components such as water, saline, glycerol, or ethanol can be included in such a composition. Additionally, auxiliary substances, such as wetting or emulsifying agents, pH buffering substances and the like, may optionally be present in such compositions. For example, carriers that have been used for oral or parenteral administration include Ringer's solution, Hank's solution, and solutions of glucose, sucrose, lactose, mannose, dextrose, dextran, mannitol, sorbitol, albumin, polyethylene glycol (PEG), phosphate, acetate, gelatin, collagen, Carbopol®, vegetable oils, and the like. These compositions may optionally include stabilizers, antioxidants, antimicrobials, preservatives, buffering agents, surfactants, and other accessory additives. Cream or ointment bases useful in formulation include lanolin, Silvadene® (Marion), Aquaphor® (Duke Laboratories), and the like. Other topical formulations include aerosols, bandages, sustained-release patches, and the like.

A "therapeutically effective amount" is that amount that is effective for production of a desired result. This amount varies depending upon the health and physical condition of the individual to be treated, the capacity of the individual's immune system to synthesize antibodies, the degree of protection desired, the formulation, the attending physician's assessment of the medical situation, the age, size, and condition of the subject, the nature and severity of the disorder to be treated, and other relevant factors. It is expected that the amount will fall in a relatively broad range that can be determined through routine trials by a qualified physician or veterinarian. Thus, for example, a therapeutically effective amount for an inflammatory response inhibitory dose can be in the range of about 50–500 µg/kg, preferably, about 100–500 µg/kg, more preferably, about 150–450 µg/kg, most preferably, about 200 µg/kg. In general terms, an effective dose of IGF-I and IGF-II will range from about 5–10 µg/kg to about 50 µg/kg to a range of 100 µg/kg to 500 µg/kg/day. Alternatively, an effective dose of IGF-I and IGF-II can range from 10–50 µg/kg, 10–500 µg/kg, 50–100 µg/kg, 100–150 µg/kg, 150–200 µg/kg, 200–400 µg/kg, 250–350 µg/kg, and 400–500 µg/kg. Such a regimen can be administered as a single dose or as multiple doses. When IGF is given as multiple doses, for purposes herein, such multiple doses can be given in a day, preferably they are given within a week, more preferably, they are given within 2 weeks, and most preferably, within a month. Optionally, IGF herein can be given until the desired response is achieved.

Alternatively, one may incorporate or encapsulate IGF in a suitable polymer matrix or membrane, thus providing a sustained-release delivery device suitable for implantation on or near the site to be treated locally. Other devices include indwelling catheters and devices such as the Alzet® minipump. Further, one may provide the compound in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences 18th edition, 1990 (Mack Pub. Co., Easton, Pa.).

The compounds of the invention may be administered by a variety of methods as conventionally known in the art suitable to attain the desired result, including for example, subcutaneously, topically, intravenously, orally, intramuscularly, intraperitoneally, intra-luminally, and intra-articularly. The preferred route of administration will depend upon the nature of the formulation and the condition to be treated. The duration of treatment may include, for example, a single dose of 25–100 µg/kg/shot, which may be administered once, or two or three times daily. The number of days of administration may be one to two days. For conditions such as rheumatoid arthritis, administration three times weekly may be appropriate, when administered intra-articularly at higher dosages of, for example, 100–500 µg/kg/dose, administered for three months. Chronic inflammatory bowel and other inflammatory diseases or conditions may require, for example, daily administration for one to six weeks, administered locally including intra-luminally to the GI tract. For systemic inflammatory response conditions, subcutaneous administration may be required at lower doses, including, for example 25–100 µg/kg/dose, for a duration depending on the severity of the condition and the responsiveness of the individual to treatment. For acute renal failure, and for acute brain or liver failure, for example, the duration of the treatment may require 4–14 days of daily administration, or 4–21 days of daily administration, or 4–28 days of daily administration. For administration to the brain, intra-ventricular administration may be required.

IGF for use herein can be made by a variety of known techniques. Thus, IGF can be isolated and purified from serum or plasma or produced by recombinant DNA techniques in microbial hosts such as bacteria or yeast or in cell cultures such as insect cell or animal cell cultures, or chemically synthesized in accordance with conventional techniques. For example, IGF can be isolated in small quantities from large volumes of plasma or serum as described in Phillips, New Engl. J. Med., (1980) 302:371–380.

IGF can also be synthesized by the solid phase method as described in Li, PNAS, (1983) 80:2216–2220. In this method, the polypeptide sequence for IGF-I can be assembled by coupling the amino acid residues.

IGF can be made by conventional recombinant DNA techniques, as described in Biochem. and Biophys. Res. Comm., (1990) 169:832–839 (IGF II) and Cell Regulation, (1990) 1:197–213, (IGF II), and Biotechnology News, (1983) 3:1–3 (IGF-I and II). For example, IGF can be produced in E. coli as a fusion protein with the trpE gene under the control of a modified tryptophan operon, as described in U.S. Pat. No. 4,738,921. Alternatively, IGF can be synthesized in E. coli under the control of the Vesicular Stomatitis Virus (VSV) promoter and protector sequences, as described in EP 478 333. The E. coli expression systems used for expression herein can be modified as described in U.S. Pat. No. 5,158,875, to include a modified positively charged leader sequence to enable proper folding of the IGF protein.

Moreover, IGF can be produced in methylotrophic yeast transformants with the IGF coding sequence linked to a signal sequence which direct secretion and proteolytic processing of the protein product. The signal sequence suitable herein includes the S. cerevisiae alpha mating factor pre-pro sequence in protease deficient P. pastoris strains, as described in WO 92/04363.

DNA constructs for production of IGF-II can be made and expressed in E. coli as described in WO 89/03423. Synthesis of recombinant IGF-II can also be achieved by following the protocol described in EP 434 605, which relates to the production of recombinant IGF-II with a covalently attached foreign moiety and lacking the N-terminal attached methionine.

IGF can also be made in yeast as described in EP 123 228 and U.S. patent application Ser. No. 06/922,199. Another method of producing IGF using recombinant DNA techniques that is suitable herein is as described in Biotechnology News, (1983) 10:1–3. IGF-I or IGF-II coding sequences can be inserted into viral or circular plasmid DNA vectors to form hybrid vectors, and the resulting hybrid vectors can be used to transform host microorganisms such as bacteria or yeast cells. The transformed microorganisms can be grown under appropriate nutrient conditions to express IGF, as described in EP 135 094.

In another context, human IGF-I and IGF-II can be expressed and secreted using a leader sequence that contains a portion of the yeast α-factor signal sequence, as described in EP 128 733.

The IGF-I herein can be expressed in any unicellular organism, including, for example, yeast cells, bacterial, insect, and mammalian cells. For example, yeast cells in which IGF-I can be expressed include Saccharomyces cerevisiae (Hinnen, PNAS, (1978) 75:1929; Ito, J. Bacteriol., (1983) 153:163; Saccharomyces carlsbergeneis; Candida albicans, Kurtz, Mol. Cell. Biol., (1986) 6:142; Candida maltosa, Kunze, J. Basic Microbiol., (1985) 25:141; Hansenula polymorpha (Gleeson, J. Gen. Microbiol., (1986) 32:3459; Roggenkamp, Mol. Gen. Genet., (1986) 202:302; Kluyveromyces fragilis, Das, J. Bacteriol., (1984) 158:1165;

*Kluyveromyces lactis*, De Louvencourt, *J. Bacteriol.*, (1983) 154:737; Van den Berg, *Bio/Technology*, (1990) 8:135; *Pichia guillerimondii*, Kunze, *J. Basic Microbiol.*, (1985) 25:141; *Pichia pastoris*, Cregg, *Mol. Cell. Biol.*, (1985) 5:3376; U.S. Pat. Nos. 4,837,148 and 4,929,555; *Schizosaccharomyces pombe*, Beach, *Nature*, (1981) 300:706; and *Yarrowia lipolytica*, Davidow, *Curr. Genet.*, (1985) 10:380471; Gaillardin, *Curr. Genet.*, (1985) 10:49; *Neurospora crassa*, Case, *PNAS* (USA), (1979) 76:5259; and filamentous fungi such as, Neurospora, Penici/lium, Tolypocladium, WO 91/00357, and Aspergillus hosts such as *A. nidulans*, Ballance, *Biochem. Biophys. Res. Comm.*, (1983) 112:284; Tilburn, *Gene*, (1983) 26:205, Yelton, *PNAS* (USA), (1984) 1981:1470, and *A. Niger*, Kelly, *EMBO J.*, (1985) 4:475–479.

IGF-I herein can also be expressed in bacterial cells including, for example, *Streptococcus spp.*, and *Streptomyces spp.*, eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescans*.

IGF-I herein can further be expressed in insect cells with a baculovirus expression system, including, for example, numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells, as described in Luckow, *Bio/Technology*, (1988) 6:47; Miller, *Genetic Engineering*, Plenum Publishing (1986) 8:277; and Maeda, *Nature*, (1985) 315:592. The vector may be a baculovirus transcriptional promoter region derived from any of the over 500 baculoviruses generally infecting insects, such as for example the Orders Lepidoptera, Diptera, Orthoptera, Coleoptera and Hymenoptera, including for example the viral DNAs of *Autographo californica* MNPV, *Bombyx mori* NPV, *rrichoplusia ni* MNPV, *Rachiplusia ou* MNPV or *Galleria mellonella* MNPV, *Trichoplusia ni*, *Rachiplusia ou*, and *Galleria mellonella*, and others as described in Smith, *Virol.*, (1978) 89:517.

IGF-I can also be expressed in mammalian host cells including, for example, expression in monkey cells, as described in Reyes., *Nature*, (1982) 297:598, cultured mouse and rabbit cells, mouse NIH-3T3 cells many immortalized cell lines available from the American Type Culture Collection (ATCC), including, for example, Chinese hamster ovary (CHO) cells, as described in Urlaub, *PNAS* (USA), (1980) 77:4216, HeLa cells, baby hamster kidney (BHK) cells, monkey kidney cells (COS), human hepatocellular carcinoma cells (e.g., Hep G2), human embryonic cell line as described in Grisham, *J. Gen. Virol.*, (1977) 36:59, mouse sertoli cells as described in Mather, *Biol. Reprod.*, (1980) 23:243, African green monkey cells, canine kidney cells, buffalo rat liver cells, human lung cells, human liver cells, and mouse mammary tumor cells, among others.

The following examples are given by way of illustration to facilitate a better understanding of the invention and are not intended to limit the invention in any way.

EXAMPLE 1

Making IGF-I

The rhIGF-I protein was synthesized by *Saccharomyces cerevisiae* strain JSC417, transformed with plasmid pYLUIGF1-24. The yeast strain JSC417, was deposited with the American Type Culture Collection (ATCC) located at 12301 Parklawn Drive, Rockville, Md. 20852, on Aug. 2, 1994 with ATCC Accession No. 74295. Strain JSC417 was derived from strain AB110. JSC417 has the following genotype: Matα, ura 3-52, leu 2, pep 4-3, his 4-580, [cir °].

Expression of rhIGF-I in *S. cerevisiae* strain JSC417 was non-constitutive and under the regulation of a hybrid ADH2-GAP promoter derived from promoter sequences of the yeast alcohol dehydrogenase as described in Beier, *Nature*, (1982) 300:724, and glyceraldehyde-3-phosphate dehydrogenase as described in EP 120 551. In addition, the rhIGF-I sequences are fused to the yeast α-factor leader which allows for secretion, and to the yeast α-factor terminator both as described in Brake, *PNAS*, (1984) 81:4642. Induction of rhIGF-I expression is achieved by maintaining low concentration of glucose in the growth medium during fermentation.

Figure 3:
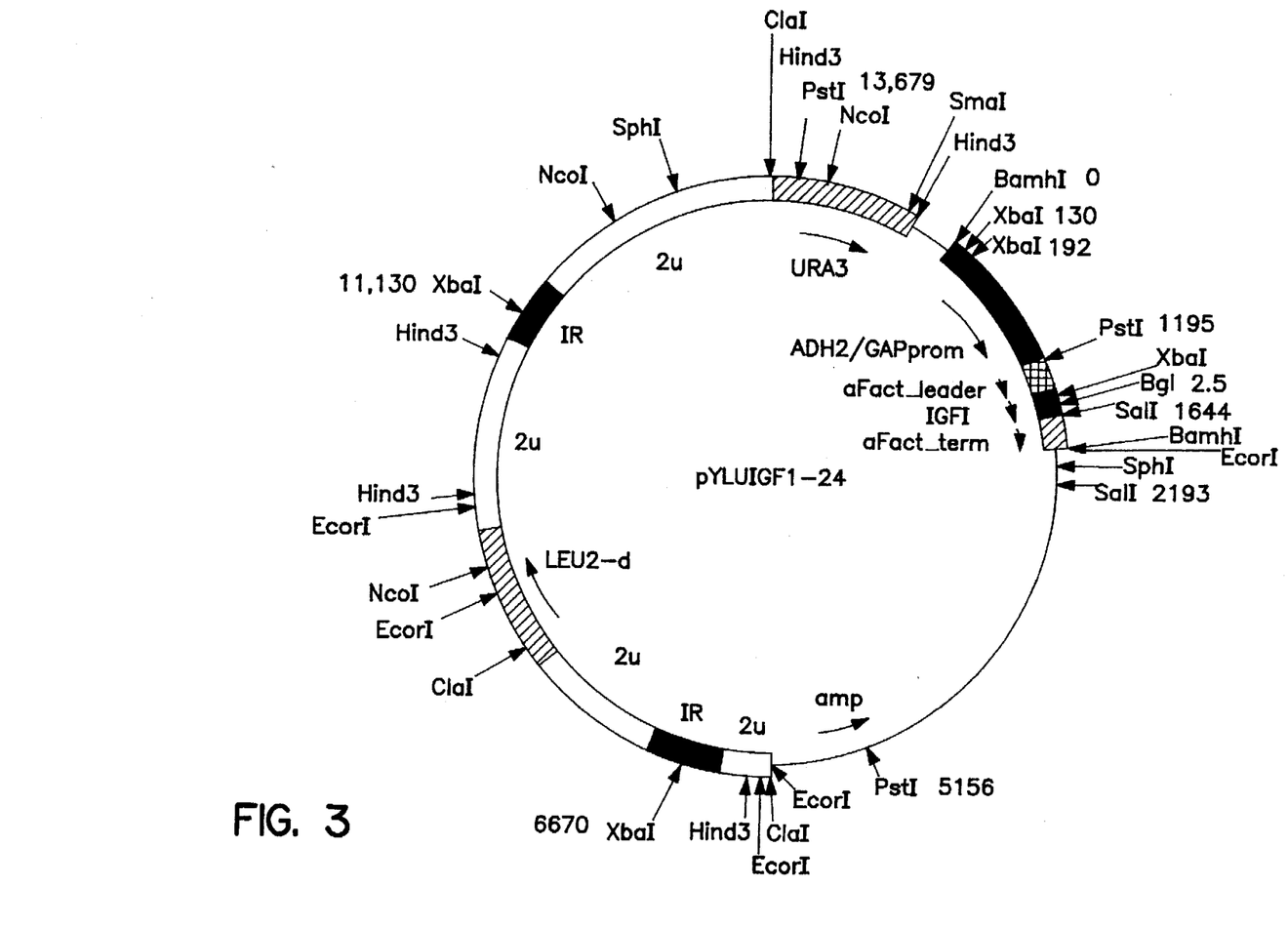
FIG. 3 depicts a plasmid map of rhIGF expression plasmid pYLUIGF1-24.

Plasmid pYLUIGF1-24 is a yeast expression vector which contains the sequence coding for rhIGF-I cloned into the BamHI site of vector pAB24, as described in Barr, *Bio/Technology*, (1987) 5:486, as well as pBR322 sequences including the ampicillin resistant (ampR) gene, 2-micron (2μ) sequences, and the yeast LEU 2 and URA 3 genes. The expression cassette for rhIGF-I consisted of (5' to 3') ADH2 regulatory sequences, a GAP promoter, α-factor leader, rhIGF-I synthetic gene and α-factor terminator, as described in EP 123 228.

The rhIGF-I gene cloned into the expression cassette was chemically synthesized using the phosphoramidite procedure as described by Urdea, *PNAS*, (1983) 80:7461, and according to the Dayhoff amino acid sequences.

*S. cerevisiae* cells were transformed with plasmid pYLUIGF1-24 following a standard protocol as described in Hinnen, *PNAS* (USA), (1978) 75:1929. Briefly, the transformation mixture was plated onto uracil-deficient selective plates that were yeast nitrogen base with amino acids containing 2% glucose and incubated for four days at 30° C. Transformant colonies were transferred into leucine-deficient, selective media with 8% glucose, and grown at 30° C. Expression of rhIGF-I was accomplished by growing the yeast transformants in uracil deficient medium with 0.4% glucose at 30° C. for 48 hours. Expression of rhIGF-I in the medium at 48 hours was analyzed by any of several standard methods including RP-HPLC, SDS-PAGE, RIA, or radioreceptor assay.

Production of rhIGF-I involves successive amplification of the yeast cells contained within the seedstock aliquot. The first amplification stage was carried out in shake flasks at a controlled temperature of 30° C. in a rotary shaker-incubator. Approximately $10^8$ cells were thawed into 500 mL of uracil- and leucine-deficient media, as described above, containing 5-8% glucose. After 25–45 hours, preferably 35±2 hours, the flask contents were transferred to a small fermentation vessel for the second stage of cell amplification. This culture was grown for 24±4 hours under controlled temperature (30° C.), aeration (1 vvm) and agitation (400–600 rpm) in 10 L of the same media used for stage I. 10–30 L of the stage II culture was transferred to a larger, production-scale fermentation vessel for the final amplication and rhIGF-I expression phase of growth. Stage III utilized a semi-defined growth media containing casein hydrolyzate, basal salts, vitamins, trace elements, and antifoam. The casein hydrolyzate employed may be any commercial brand with a composition of at least 5% amino-nitrogen, at least 10% total nitrogen, not more than 20% ash, but preferably would have a composition comparable to that of N-Z-Amine HD (Quest). The antifoam employed may be any of several commercially available polyalcohol- or silicon-based compounds. The media is listed in Table A below. The fermentation was carried out at constant 30° C., pH 6 (by addition of 50% sodium hydroxide or 75% phosphoric acid), aeration (0.8 vvm), pressure (5–12 psig), and glucose feed rate with constant agitation. The fermentation is known to those skilled in the art as a fed-batch mode of operation, so-called because the fermentor is initially filled to less than capacity, allowing for the addition of a suitable amount of a glucose feed solution with a concentration of 25–50% w/v. Typically, 800–900 kg glucose is added to the fermentor over the duration of the run at a rate of addition that depends on yeast cell density and residual glucose concentration. Typically, glucose is added at 500 g/min for the first 26 h, at 1000 g/min for the next 24 h, and finally at 500 g/min until completion. Cell growth concomitant with product expression occurs once the media becomes depleted of excess glucose, and may continue until the culture reaches the desired cell density of approximately 35 gDCW/L.

rhIGF-I was recovered from the cell cultures using conventional techniques. At the completion of fermentation, the pH of the fermentor culture was raised to a range of pH 9–10, pH 10.1–10.3, pH 10.4–10.6, pH 10.6–10.8, pH 10.9–10.11, or pH 11–12 for at least 30 minutes. Prior to cell removal 50% sodium hydroxide is added to the fermentor to raise the pH of the whole culture to with a range of pH 9–10, pH 10.1–10.3, pH 10.4–10.6, pH 10.6–10.8, pH 10.9–10.11, or pH 11–12 for 0.5 to 4 h (preferably pH 10.2 for at least 0.5 h). Afterwards the whole yeast were separated from the product-containing spent media by continuous centrifugation. After collection the supernatant was readjusted to with a range of pH 3–4, pH 5–6 or pH 6–7 (preferably pH 4) with 75% phosphoric acid, and filtered using microporous tangential flow filtration prior to adsorbing on a cation exchange resin. The column was washed with 20 mM acetic acid and 100 mM potassium borate/0.1 mM EDTA buffers, and eluted with a 100 mM potassium borate/0.1 mM EDTA/300 mM potassium chloride buffer at pH 8.7.

Standard hydrophobic interaction chromatography (HIC) was used for primary purification of rhIGF-I. Ammonium sulfate precipitation and microporous tangential flow filtration was used to remove yeast contaminants. After washing the precipitate with ammonium sulfate, sodium acetate and EDTA buffer at pH 4, the material was loaded onto the HIC matrix and eluted with linear decreasing gradient of 0.9 to 0.5M ammonium sulfate. Eluted protein at pH 4 was concentrated 20-fold and the buffer was exchanged using a 5000 MWCO tangential flow ultrafiltration membrane. The diafiltration agents employed were high purity water followed by 20 mM acetic acid.

Standard reverse-phase high performance liquid chromatography (RP-HPLC) was used to remove product-related species from the authentic rhIGF-I. The 5K concentrate was loaded onto a suitable C8 matrix and eluted with a linear increasing gradient of 10% to 50% acetonitrile in a pH 6.8 ammonium acetate buffer.

EXAMPLE 2

Use of IGF-I to Reduce Inflammatory Response Associated with Ischemic Injury

It is known that ischemic acute tubular necrosis (ATN) induces inflammation, MHC and cytokine expression. Here we show that IGF-I reduced cytokine and MHC induction after induction of ATN. The human IGF-I (huIGF-I) was administered to mice after ATN induction. The degree of inflammation was assessed by the degree of major histocompatibility complex (MHC) expression and cytokine expression. ATN was produced in mice by clamping the left renal pedicle for 60 minutes. MHC expression was quantified by the binding of radiolabelled monoclonal antibodies (mAbs) (RIA). Steady state mRNA levels for IL-2, IL-10, GM-CSF and IFN-γ, were assessed by RT-PCR and for TGF-β-1, TNF-α and ppEGF by Northerns. In the absence of IGF-I, MHC Class I and Class II mRNA and product were increased, for two weeks for Class I and for 5 weeks for Class II. In the ischemic kidneys, IL-2, IL-10, GM-CSF, IFN-γ, TNF-α, TGF-β-1 mRNA were induced, whereas ppEGF mRNA was greatly decreased. Administration of rhIGF-1, 25 μg s.c. daily starting 1 hour after reperfusion, reduced MHC expression and cytokine mRNA induction after ischemic injury, assessed at day 5. Results are shown in Tables I–VI.

Male BALB\c and CBA mice obtained from Jackson laboratories (Bar Harbor, Me.) were operated on at 6–15 weeks of age. They were anesthetized with 2,2,2-tribromoethanol in tert-butyl alcohol (Avertin) by intraperitoneal injection. The left renal pedicle was identified through a midline incision and occluded with a micro-bulldog clamp for 60 minutes. Before closure the kidney was inspected to ensure reperfusion, and the abdominal cavity was filled with warm saline. Control mice underwent a simple laparotomy under identical conditions. The mice were harvested at 4 and 5 days postoperatively. Each group contained between 4 and 8 animals at harvesting time. No thrombosis was seen, even though neither heparinization nor renal flushing were used. ATN was confirmed in these experiments with tissue staining, using HE and PAS, of two animals randomly selected in each group. In the first two experiments rhIGF I was administered according to the following protocol, (n) being the number of mice in each group:

| Exp. 1 | (n) | Exp. 2 | (n) |
|---|---|---|---|
| 1. CBA/J + 0.9% NaCl | (8) | 1. CBA/J + 0.9% NaCl | (6) |
| 2. CBA/J + rhIGF I | (8) | 2. ATN day 5 + 0.9% NaCl | (8) |
| 3. ATN day 4 + 0.9% NaCl | (5) | 3. ATN day 5 + rhIGI I | (8) |
| 4. ATN day 4 + .9% rhIGF | (4) | | |

Human IGF-I diluted in 0.9% NaCl was administered s.c.; 25 μg at 2, 24, 48, 72 and 96 hours after surgery. The dose was selected based on the dose used in the rat studies in which rhIGF-I was found to accelerate renal recovery, as described in Miller, *PNAS* (USA), (1992) 89:11876, and Ding, *J Clin Invest*, (1993) 91:2281.

Monoclonal antibodies were prepared as ascites tumors or as supernatants from hybridomas supplied by American Type Culture Collection (Rockville, Md.). They were purified over a protein A column and adjusted to a protein concentration of 1 mg/ml. The anti-class I, anti-H-2K(k), were Ig class IgG(2a) and the anti-class II, anti-I-A(k) were IgG(2b). The rat anti-mouse H-2 haplotypes (M1) and anti-I-A (b,d,q haplotypes) and I-E(dk) (M5) were IgG(2a) and IgG(2b), respectively. The goat anti-rat and goat anti-mouse peroxidases were polyconal F(ab')2 fragments of IgG heavy and light chains. Radioiodination with $^{125}$I was performed by Iodogen method as described in Salacinski, *Anal Biochem*, (1981) 117:136.

The RIA technique employed was previously reported in Cockfield, *J Immunol*, (1989) 142:1120. Accordingly, tissue homogenates were prepared, aliquoted in 5 mg samples, and spun. The tissue pellets were incubated with $^{125}$I-labelled anti-MHC mAb for 1 hour. After washing, the pellets were counted in a gamma counter to obtain the number of counts remaining bound to the tissue pellet. All samples were tested in triplicate. Raw counts from experimental tissues were corrected for nonspecific binding by subtracting the counts bound to 5 mg of tissue from an irrelevant strain. Specific binding, demonstrated both directly and by competitive inhibition, is observed only in mice expressing the particular MHC haplotype and cannot be explained by FcR binding. The differences between left (clamped) and right (control) kidneys were compared by one-way analysis of variance (Anova). All results are expressed as mean±SEM.

Total RNA was extracted from pooled samples according to a modification of the method described by Chirgwin, *Biochemistry*, (1979) 18:5294. Tissues were homogenized with a polytron in 4M guanidinium isothyocyanate, and the RNA was pelleted through a 5.7M $CsCl_2$ cushion as described in Glisin, *Biochemistry*, (1974) 13:2633. RNA concentrations were determined by absorbance at 260 nm. Northern blots were prepared using 25 to 35 µg of total RNA electrophoresed through a 1.5% agarose gel in the presence of 2.2M formaldehyde, with transfer to nitrocellulose filters. Blots were hybridized with $^{32}$P-labelled cDNA probes for the HLA-A3 gene (Class I), α-chain of I-A (Class II), ppEGF, TNF-α and TGF-β-1. Kodak X-Omat AR film was exposed to each blot, with an intensifying screen at −70° C.

Total RNA prepared by the guanidinium-cesium chloride method was reverse transcribed in a 10 µl reaction containing 5 ng/µl IFN-γ specific downstream primer, 5 U/µl moloney murine leukemia virus reverse transcriptase (Superscript; BRL), standard reaction buffer, and nucleotides. The cDNA product was then amplified in a 50 µl reaction with standard PCR reaction buffer, BSA, the appropriate primers and 0.01 U/µl Taq polymerase (BRL), by using a thermocycler. A $MgCl_2$ titration curve had previously established that 2.5 mM $MgCl_2$ was the optimal concentration for this primer pair. The cycler program was one of the many standard ones in the art of PCR, with an initial denaturation, annealing and extension times and temperatures. The RT-PCR product was run on a 1.5% agarose gel, transferred to a nylon membrane, and hybridized with a $^{32}$P-labelled IFN-γ cDNA probe. The primers used were based on known sequence information as described in Gray, *PNAS* (USA) (1983) 80:5842, and were located on either side of an intron to ensure that the amplified product was derived from RNA and not contaminating genomic DNA. The strategy for RNA reverse-transcription, and DNA amplification for IL-2, IL-10 and GM-CSF was the same as used for IFN-γ.

The cDNA probe used for murine IFN-γ was a cDNA fragment of Aα,d inserted at the PstI site of pBR322, for detecting transcripts of the α chain of I-A; a 1.5 kB cDNA fragment of the HLA-A3 gene inserted into pEMBL8 was used to detect Class I transcripts; a 0.96 kB cDNA fragment of murine ppEGF inserted into the PstI site of pBR322 was used to probe for ppEGF; a 2.13 kB fragment of the human TGF-β-1 mRNA; the GM-CSF probe was a cDNA fragment of the gene; the IL-10 probe was an oligomer of +213 to +253 of the gene. All probes were $^{32}$P-labelled by the random priming method of Feinberg and Volgelstein, *Anal Biochem*, (1983) 132:6.

One of the inventors had previously established that unilateral ischemia in the mouse is well tolerated and is followed by complete parenchymal recovery as described in Shoskes, *Transplantation*, (1990) 49:201, and Shoskes, *Transplant Proc*, (1991) 23:599. Here, histological evidence of acute tubular necrosis (ATN) was seen in the ischemic kidney by 12 hours and persisted in severe form for 3–5 days. Interstitial hypercellularity was readily apparent in the left kidneys around day 7, with frequent progression to an interstitial mononuclear cell infiltrate by days 14 to 35. Right (control) kidneys were histologically normal. Serum creatinine and blood urea levels at the time of harvesting in selected animals from control and experimental groups showed no detectable elevation.

Figure 1A:
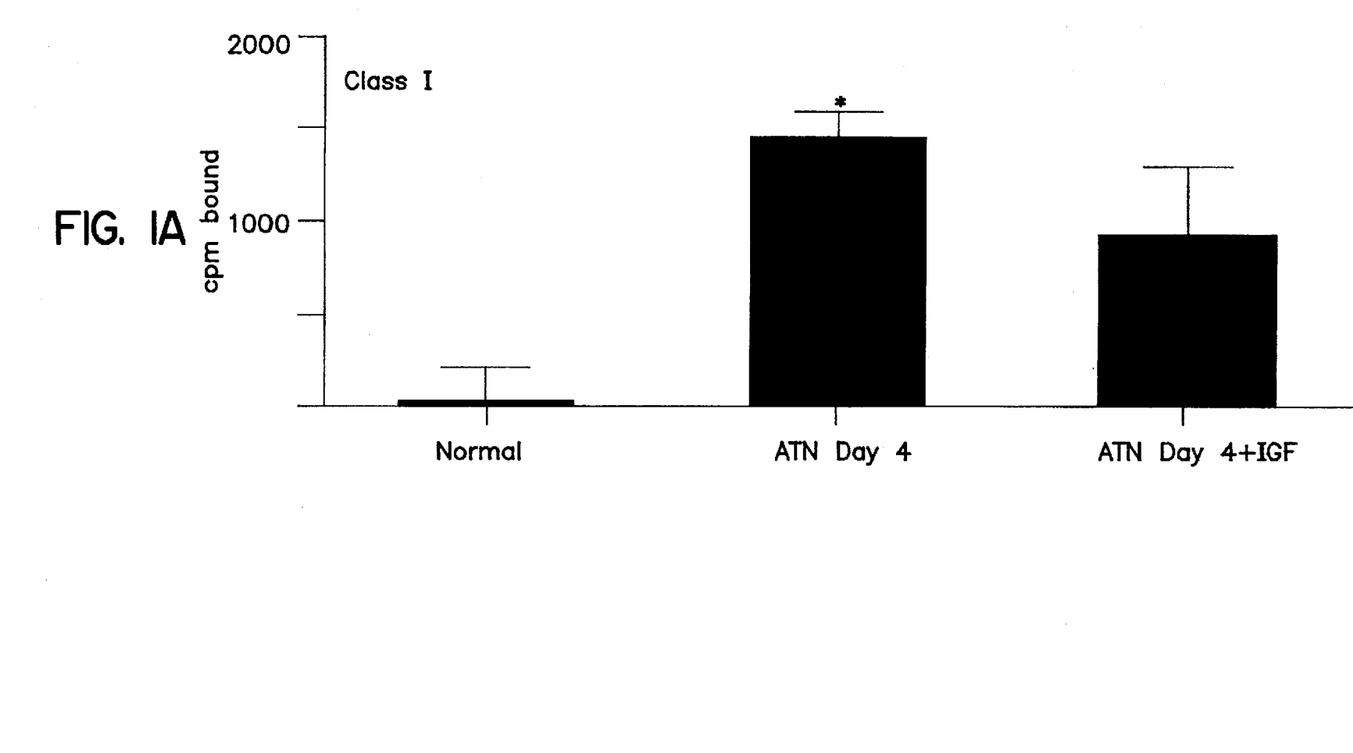
FIGS. 1A and 1B shows the effect of recombinant human IGF-I (rhIGF) on MHC Class I and II expression by RIA on ATN induced group day 4.
Figure 1B:
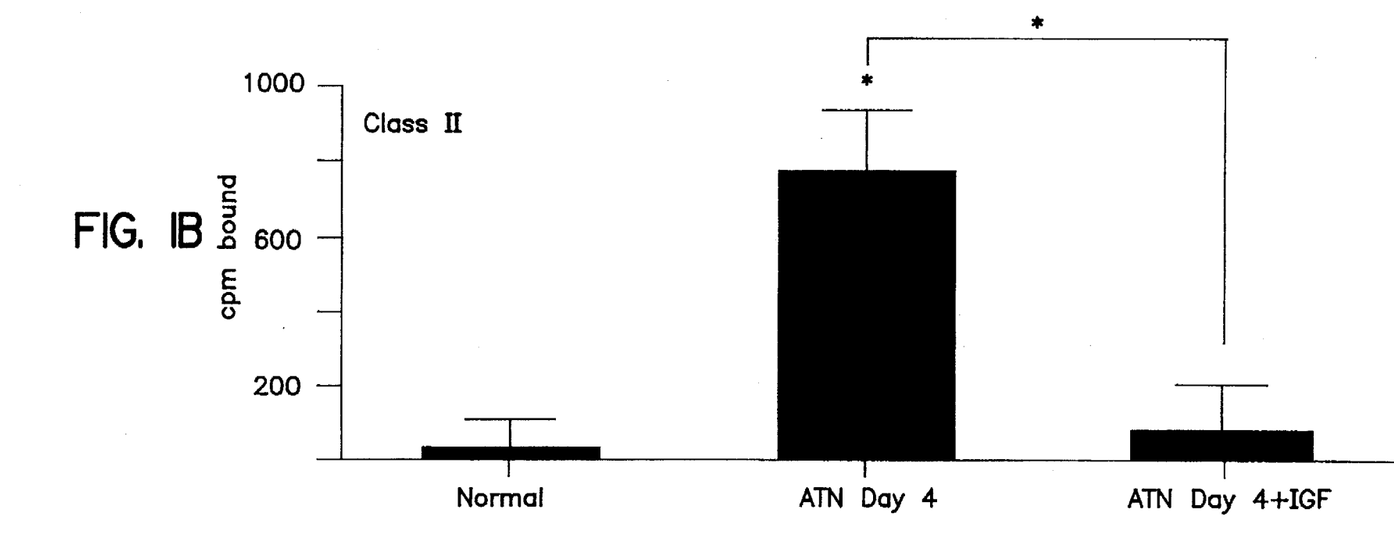
Figure 2A:
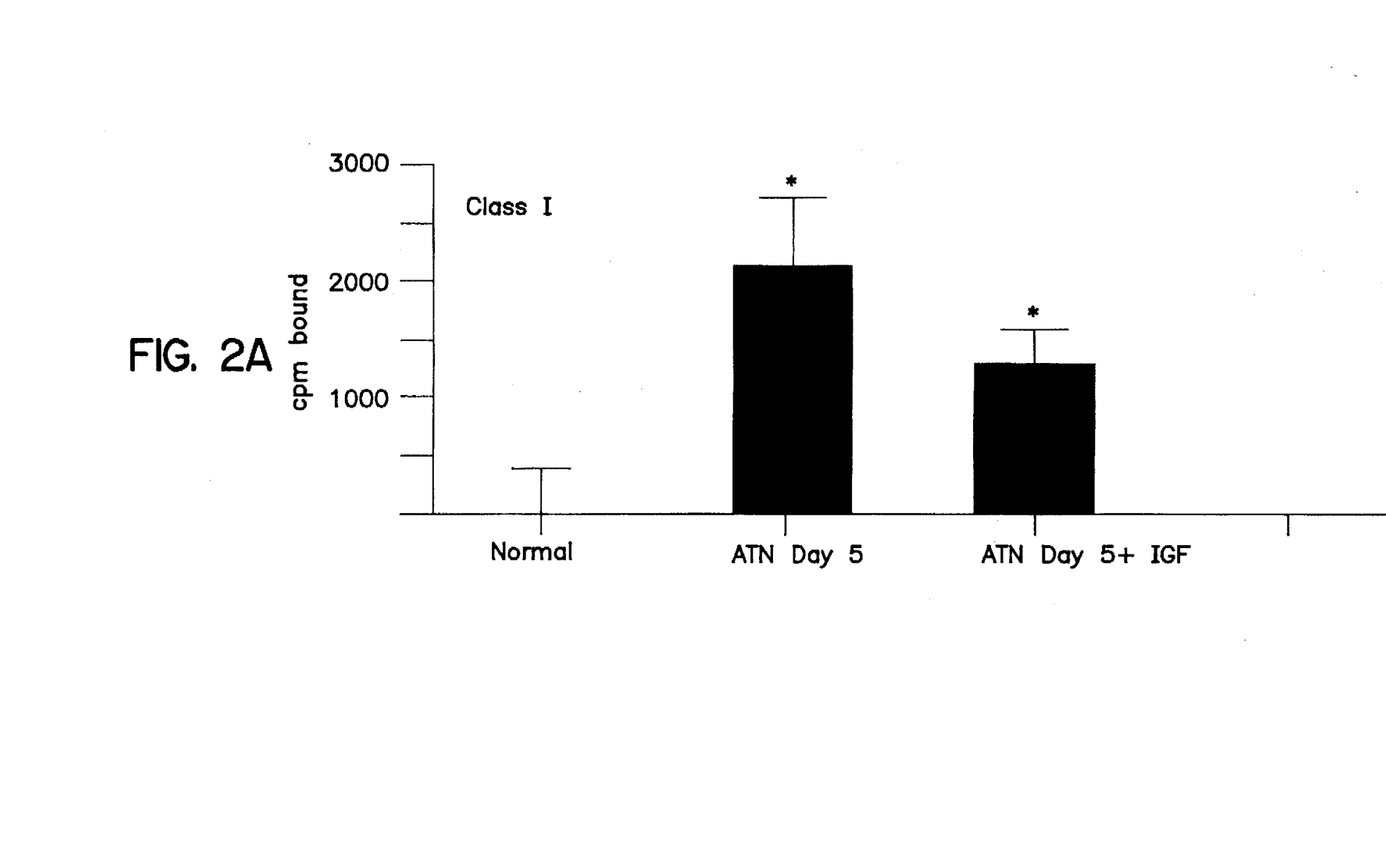
FIGS. 2A and 2B shows the effect of rhIGF MHC Class I and II expression by RIA on ATN induced group day 5.
Figure 2B:
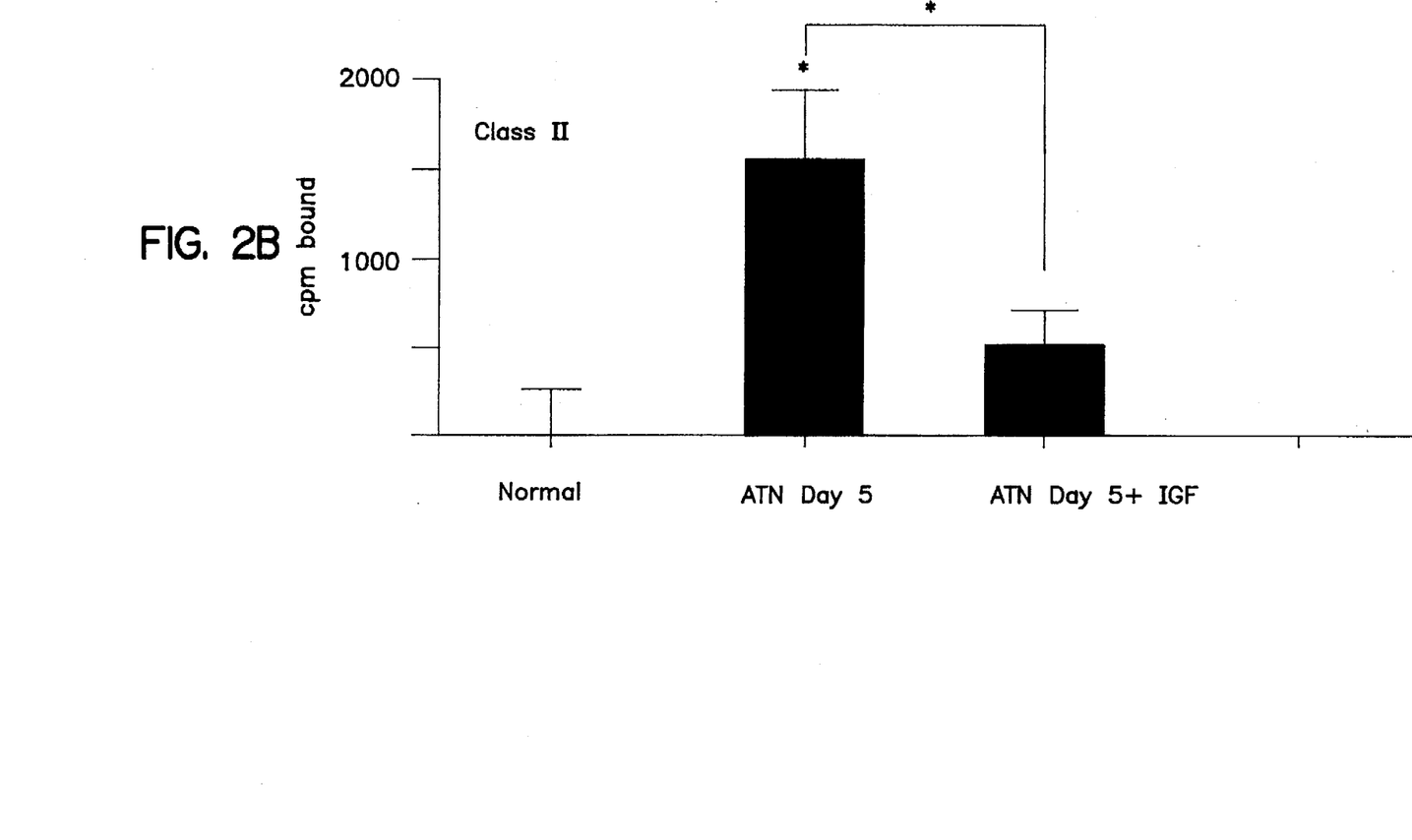

Treatment with rhIGF-I reduced MHC induction after induction of ATN. Northern blot analysis performed with ATN or normal kidneys, using total RNA extracted from a pool of three kidneys, show increased Class I and II mRNA expression in ATN kidneys. The inventors found a reduction of MHC gene induction after rhIGF-I treatment (Table I). MHC Class I and II gene induction was also studied at the protein level using radiolabelled monoclonal antibodies (RIA) against Class I and II (Table II and III and Graphs 1 and 2 shown in FIGS. 1 and 2, respectively). Administration of rhIGF-I reduced, by approximately 60–70%, Class I and II product expression. Class I was detected mainly in the basolateral aspect of tubular cells at the outer stripe of the outer medulla with a focal and segmental distribution and was reduced by treatment with rhIGF-I (Tables IV and V). Class II expression, as the inventors had previously described, was not detected by staining at days 4 and 5.

The inventors also found that rhIGF-I reduced cytokine gene induction after induction of ATN. The inventors found that IL-2, IL-10, GM-CSF, IFN-γ, TNF-α and TGF-β-1 and a marked reduction of ppEGF genes in ATN kidneys. Administration of rhIGF-I reduced the induction of all cytokine genes and reduced the extent of ppEGF mRNA decrease induced by ATN (Table VI). The ability of rhIGF to reduce the cytokine and inflammatory response may reflect (a) reduction in the extent of injury; (b) increased spead of recovery from injury; (c) a direct inhibition of the cytokine and inflammatory response; and (d) a combinantion of these mechanisms.

TABLE I

MHC Gene Induction After Ischemic Injury - Effect of rhIGF-I

|  | Class I | Class II |
|---|---|---|
| Normal | − | − |
| ATN day 5 | +++ | +++ |
| ATN day 5 + rhIGF-I | ++ | ++ |

Results are expressed as the difference between left (ischemic) and right kidney (from + to +++) using Northern blot analysis.

TABLE II

Ischemia-Induced MHC Expression - Effect of rhIGF-I

|  | Class I | Class II |
|---|---|---|
| Normal | −222.3 ± 412.6 | −61.2 ± 258.9 |
| ATN day 5 | 2156 + 618.2 | 1577.3 ± 407.8 |
| ATN day 5 + rhIGF-I | 1258.4 + 429.2 | 498.7 ± 536.9 |

Results are expressed as the difference between left (ischemic) and right kidney using radiolabelled mAbs against MHC Class I and II products (RIA) (Mean cpm ± SEM).

TABLE III

Ischemia-Induced MHC Expression - Effect of rhIGF-I

|  | Class I | Class II |
|---|---|---|
| Normal | 41.5 ± 164.7 | 35.7 ± 75 |
| ATN day 4 | 1447.8 ± 177 | 757.2 ± 204.8 |
| ATN day 4 ± rhIGF-I | 883.6 ± 460 | 97.7 ± 132.3 |

Results are expressed as the difference between left (ischemic) and right kidney using radiolabelled mAbs against NHC Class I and II products (RIA) (Mean cpm ± SEM).

TABLE IV

Ischemia-Induced Renal MHC Expression - Effect of rhIGF-I

|  | Class I | | Class II | |
|---|---|---|---|---|
|  | Tubular | Interstitial | Tubular | Interstitial |
| ATN day 4 | +++ | − | − | − |
| ATN day 4 + rhIGF-I | ++± | − | − | − |

Results are expressed as intensity of immunoperoxidase straining (from − to ++++) using anti-Class I and II mAbs.

TABLE V

Ischemia-Induced Renal MHC Expression - Effect of rhIGF-I

|  | Class I | | Class II | |
|---|---|---|---|---|
|  | Tubular | Interstitial | Tubular | Interstitial |
| ATN day 5 | +++ | − | ±/+ | − |
| ATN day 5 + rhIGF-I | ± | − | −/± | − |

Results are expressed as intensity of immunoperoxidase straining (from − to ++++) using anti-Class I and II mAbs.

TABLE VI

Cytokine Gene Induction After Ischemic Injury - Effect of rhIGF-I

|  | IL-10 | GM-CSF | IFN-γ | TNF-α | TNF-β-1 | ppEGF |
|---|---|---|---|---|---|---|
| Normal | − | − | ± | − | − | − |
| ATN day 5 | +++ | +++ | +++ | +++ | +++ | − |
| ATN day 5 + rhIGF-I | ++ | − | ± | ++ | ++ | − |

Results are expressed as the difference between left (ischemic) and right (normal) kidney (from + to +++) using RT-PCR for IL-10, GM-CSF, IFN-γ and Northern blot analysis for TNF-α, TGF-β-1, and ppEGF.

The patents, patent applications and publications cited herein are incorporated by reference.

What is claimed:

1. A method for inhibition of organ rejection after transplantation in a mammal, wherein the transplanted organ is selected from the group consisting of heart, lung, liver and pancreas, said method comprising administering thereto a therapeutically effective amount of IGF.

2. The method of claim 1, wherein the IGF is IGF-I.

3. The method of claim 1, wherein at least one dose of IGF is administered at a time selected from the group consisting of:

a) prior to transplantation;

b) during transplantation; and c) after transplantation.

4. The method of claim 3, wherein IGF is administered after transplantation at a time selected from the group consisting of:

a) immediately after transplantation;

b) within one hour after transplantation;

c) within one day after transplantation;

d) within one week after transplantation;

e) within one month after transplantation; and f) within one year after transplantation.

5. The method of claim 1, wherein IGF is administered either intravenously, subcutaneously, intramuscularly, or intra-articularly.

6. The method of claim 1, wherein IGF is administered as multiple doses for about a year.

* * * * *